(12) United States Patent
Wang et al.

(10) Patent No.: US 7,645,498 B2
(45) Date of Patent: Jan. 12, 2010

(54) BALLOON CATHETER FORMED OF RANDOM COPOLYMERIZED NYLONS

(75) Inventors: Lixiao Wang, Long Lake, MN (US); Ping Huang, Plymouth, MN (US)

(73) Assignee: ev3 Inc., Plymouth, MN (US)

( * ) Notice: Subject to any disclaimer, the term of this patent is extended or adjusted under 35 U.S.C. 154(b) by 521 days.

(21) Appl. No.: 11/545,441

(22) Filed: Oct. 10, 2006

(65) Prior Publication Data

US 2007/0106212 A1 May 10, 2007

Related U.S. Application Data

(60) Provisional application No. 60/724,756, filed on Oct. 7, 2005.

(51) Int. Cl.
*B29D 22/00* (2006.01)
*B29D 23/00* (2006.01)
*B32B 1/08* (2006.01)

(52) U.S. Cl. .................. 428/35.7; 428/35.2; 428/474.4; 428/475.5; 604/96.1; 604/104; 606/194

(58) Field of Classification Search ................ 428/35.7, 428/35.2, 474.4, 475.5; 604/96.1, 104; 606/194, 606/192
See application file for complete search history.

(56) References Cited

U.S. PATENT DOCUMENTS

| | | | |
|---|---|---|---|
| 4,906,244 A | 3/1990 | Pinchuk et al. |
| 5,108,415 A | 4/1992 | Pinchuk et al. |
| 5,156,612 A | 10/1992 | Pinchuk et al. |
| 5,236,659 A | 8/1993 | Pinchuk et al. |
| 5,304,197 A | 4/1994 | Pinchuk et al. |
| 5,356,591 A | 10/1994 | Pinchuk et al. |
| 5,449,371 A | 9/1995 | Pinchuk et al. |
| 5,556,383 A | 9/1996 | Wang et al. |
| 5,738,653 A | 4/1998 | Pinchuk et al. |
| 5,830,182 A | 11/1998 | Wang et al. |
| 5,951,941 A | 9/1999 | Wang et al. |
| 6,110,142 A | 8/2000 | Pinchuk et al. |
| 6,146,356 A | 11/2000 | Wang et al. |
| 6,171,278 B1 | 1/2001 | Wang et al. |
| 6,406,457 B1 | 6/2002 | Wang et al. |
| 6,500,146 B1 | 12/2002 | Pinchuk et al. |
| 6,500,148 B1 | 12/2002 | Pinchuk et al. |

*Primary Examiner*—Michael C Miggins
(74) *Attorney, Agent, or Firm*—Rissman Hendricks & Oliverio, LLP

(57) ABSTRACT

A catheter having a balloon comprised of a polymer material comprising first monomer units of an alkyl amide having 2 to 6 carbon atoms and second monomer units of an alkyl amide having 7 to 12 carbon atoms. The first and second monomer units are copolymerized with each other in a random fashion to form a random copolyamide polymer.

13 Claims, 1 Drawing Sheet

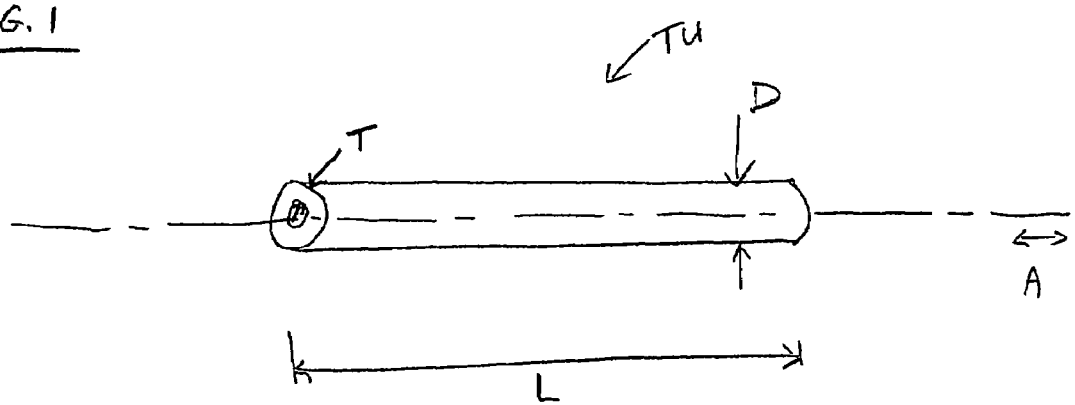
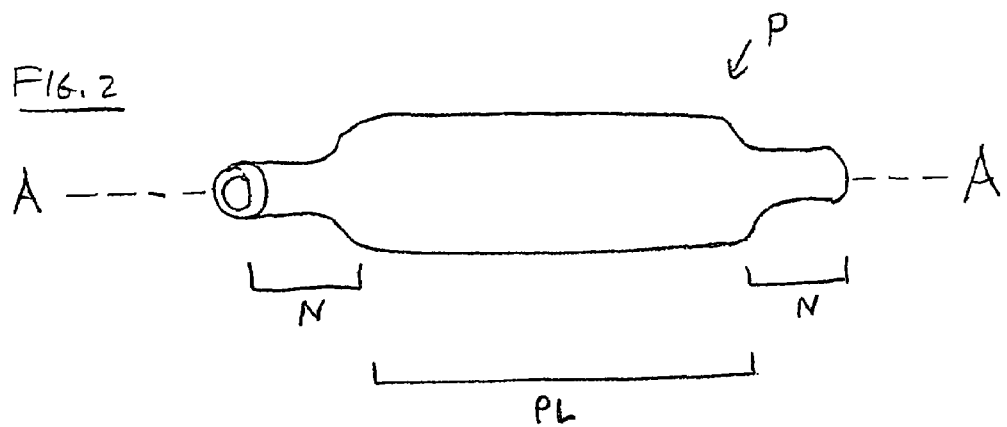
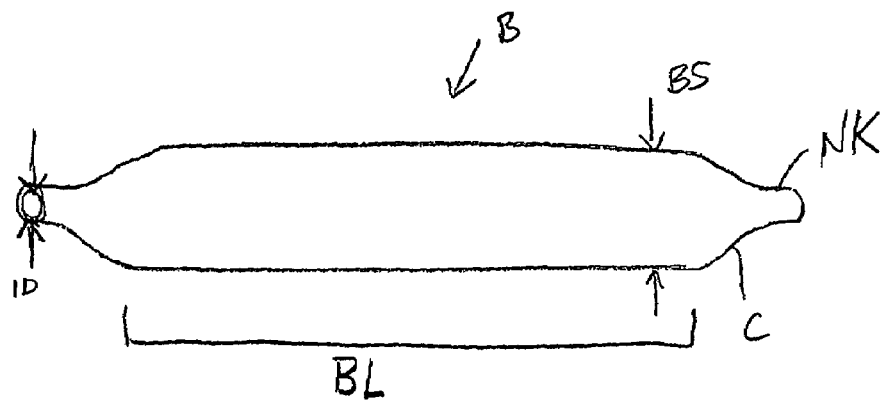

BALLOON CATHETER FORMED OF RANDOM COPOLYMERIZED NYLONS

RELATED APPLICATION

This application claims the benefit of priority under 35 U.S.C. Sections 119 and/or 120 to provisional patent application Ser. No. 60/724,756 filed Oct. 7, 2005, the entire subject matter of which is hereby incorporated by reference.

BACKGROUND

Balloon catheters having balloons manufactured from nylon materials alone or in combination with other materials are well known in the art. For example balloon materials comprised of copolymers of polyamide are disclosed in U.S. Pat. Nos. 4,906,244; 5,108,415; 5,156,612; 5,236,659; 5,304,197; 5,356,591; 5,449,371; 5,738,653; 6,110,142; 6,500,146; 6,500,148 and of copolymers of polyamides and polyether are disclosed in U.S. Pat. Nos. 5,556,383, 5,830,182, 5,951,941, 6,146,356, 6,171,278 and 6,406,457.

Catheter balloons have thin walls because the balloon's wall and waist thicknesses limit the minimum diameter of the distal end of the catheter and therefore determine the limits on vessel size treatable by the method and the ease of passage of the catheter through the vascular system. High strength is necessary because the balloon must not burst under the high internal pressures necessary to open a blood vessel. The balloon must have some elasticity so that the inflated diameter can be controlled, so as to allow the surgeon to vary the balloon's diameter as required to treat individual lesions, but that elasticity must be relatively low so that the diameter is easily controllable. Small variations in pressure must not cause wide variation in diameter.

While angioplasty balloons are considered inelastic relative to balloons used in most other applications, there is in the art a general classification of such balloons based on their expandability or compliance relative to each other. "Compliant" balloons are more distensible, having distensions generally in the range of 16-40% and typically about 21% over a 6-14 atm pressure range. Maximum distensions, i.e. distension from nominal diameter to burst, of various balloon materials may be significantly higher than the distension percentages discussed above because wall strengths, and thus burst pressures, vary widely between balloon materials. The 6-14 atmosphere (atm) inflation range is used in the present application to allow direct comparison of the compliance attributes of various balloons.

The strongest balloons are the most inelastic, being made of highly orientable polymers such as polypropylene, polyethylene terephthalate or other phthalate polyesters or copolyesters, and nylons. Tensile wall strengths are commonly 20,000-50,000 psi. Commercial angioplasty balloons made of such materials with nominal diameters in the range of 1.5-4.5 mm have distensions in the non-compliant to semi-compliant range and can often be rated to pressures of 16 atm or higher without risk of bursting (actual burst pressures may exceed 20 atm). Generally, however, as compliance increases the wall strength decreases. Other semi-compliant and compliant balloons are made of less highly orientable polymers such as ethylene-vinyl acetate, polyvinyl chloride, olefin copolymers and ionomer resins. The wall strengths of balloons made from these less orientable materials are still lower than those made from the highly orientable polymers, commonly in the range of 6,000-15,000 psi, resulting in lower rated maximum inflation pressures of 9-10 atm.

The particular distension and maximum pressure attributes of a balloon are also influenced both by polymer type and by the conditions under which the balloon is blown. Angioplasty balloons are conventionally made by blowing a tube of polymer material at a temperature above its glass transition temperature.

For any given balloon material, there will be a range of distensions achievable depending on the conditions chosen for the blowing of the balloon. In U.S. Pat. No. 4,906,244 to Pinchuck there are described balloons of nylon (i.e. aliphatic polyamide) materials, such as nylon 12, nylon 11, nylon 9, nylon 6/9 and nylon 6/6. It has also been suggested to prepare balloons of thermoplastic elastomers in U.S. Pat. No. 4,254,774 to Boretos, and polyamide elastomers have been mentioned among a number of possible balloon materials suggested in U.S. Pat. No. 5,250,069 to Nobuyoshi, et al, but there are many of such thermoplastic elastomer polymers and before the invention hereof it has been expected that performance of balloons made from these materials would not be generally any better than conventional thermoplastic polymers such as polyethylene ionomer, polyvinyl chloride, polyethylene or ethylene-vinyl acetate. In U.S. Pat. No. 5,290,306 polyester ethers and polyetheresteramide polymers of Shore D hardness less than 55 have been proposed for use as a sleeve or co-extruded outer layer to a balloon of a biaxially oriented nylon or polyethylene terephthalate (PET) material, so as to provide the balloon with improved softness and pin-hole and abrasion resistance.

Polyurethane block copolymers having flexural modulus of about 190,000 and an ultimate elongation of 250% are disclosed as balloon materials in EP 0592885 and mention is made of also using polyester block copolymers or polyamide block copolymers but no suggestion is made that such alternative copolymers could be usefully employed if their flexural modulus was substantially lower or their ultimate elongation was substantially higher than the disclosed polyurethane block copolymers.

SUMMARY OF INVENTION

Random copolymers of blocks of amide monomer units of different carbon chain length and blends of such copolymers provide a compliance, expandability, distension and wall strength desirable for a variety of blood vessel treatment applications. The structure of the polymer backbone of the invention described is comprised of differently sized amide monomer units and blocks of differently sized monomer units.

In accordance with the invention there is provided a catheter having a F balloon comprised of a polymer material comprising first monomer units of an alkyl amide having 2 to 6 carbon atoms and second monomer units of an alkyl amide having 7 to 12 carbon atoms, wherein the first and second monomer units are copolymerized with each other in a random fashion to form a random copolyamide polymer, the polymer material being formed into a tubular body, the body being stretched about two to about 4 times its relaxed length in the axial direction and blown about 4 to about 8 times its relaxed radius in a radial direction.

One or more of the first monomer units can be substituted with between 1 and 5 halogen, amine, nitro and phospho functions and one or more of the second monomer units can be substituted with between 1 and 5 halogen, amine, nitro and phospho functions.

One or more of the first and/or second monomer units can include an unsaturated moiety such as a vinyl function and such monomer units are included within the definition of "alkyl" as that term is used herein.

The first monomer or the second monomer units can be straight chained or branched. The molar ratio of first to second monomer units is preferably between about 20 and about 80 percent and preferably greater than about 60 percent.

Further in accordance with the invention there is provided a catheter having a balloon comprised of a polymer material comprising first blocks of a homopolymer of monomer units of an alkyl amide having 2 to 6 carbon atoms and second blocks of a homopolymer of monomer units of an alkyl amide having 7 to 12 carbon atoms, wherein the first and second blocks are copolymerized with each other in a random fashion to form a random block copolyamide polymer, the polymer material being formed into a tubular body, the body being stretched about two to about 4 times its relaxed length in the axial direction and blown about 4 to about 8 times its relaxed radius in a radial direction.

The surfaces of the balloons may be coated with one or more layers of materials that contain a biologically active ingredient such as heparin, paclitaxel, rapamycin, salicylic acid, morphine and analogs and derivatives of all of the foregoing. Such layers or coatings typically comprise an elastically deformable polymeric material such as a silicone, A Teflon or Teflon related substance or a biodegradable polymeric material such as a lactide based material. Alternatively, the surface of the balloon material may be treated with a biologically active substance such that the active substance is adhered or covalently bonded directly to the surface of the balloon.

Further in accordance with the invention there is provided a method of forming a balloon for a catheter comprising selecting a polymer material comprising first blocks of monomer units or a homopolymer of monomer units of an alkyl amide having 2 to 6 carbon atoms the polymer material also comprising second blocks of monomer units or a homopolymer of monomer units of an alkyl amide having 7 to 12 carbon atoms; wherein the first and second blocks are copolymerized with each other in a random fashion to form a random block copolyamide polymer; extruding and forming the polymer material into a balloon of selected length and configuration and maximum burst pressure resistance.

BRIEF DESCRIPTION OF THE DRAWINGS

FIG. 1 is an isometric view of one embodiment of tubing to be formed into a balloon for a catheter according to the invention;

FIG. 2 is an isometric view of a parison formed from the tubing of FIG. 1;

FIG. 3 is an isometric view of a catheter balloon formed from the parison of FIG. 2.

DETAILED DESCRIPTION OF INVENTION

Random copolymers of a nylon having 2-6 carbon atoms in its amide backbone and a nylon having 7-12 carbon atoms in its amide backbone are preferred for use in forming the material of the balloon of the catheters of the invention. In particular, random copolymers of nylon 6 and nylon 12 are most preferred where the weight ratio of the two polymers ranges between 20/80 and 80/20.

Most preferably the polymer materials comprise blocks that linked solely by amide linkages. The polymer materials preferably have a melt temperature of less than about 200 degrees Centigrade. Polymer materials suitable for making tubing are available from UBE Industries, Ltd. Typical nylons such as UBE nylon grade 7128B, grade 7115U, grade 7024B and grade 7034B and blends thereof in selected amounts can be used as the balloon starting material. Polymer pellets of the selected polymer materials are typically first dried to reduce moisture content to less than 0.10% by weight prior to extrusion. Once the polymer pellets have been sufficiently dried, they are extruded into tubing TU (FIG. 1) of preselected diameter D and wall thickness T using an appropriately designed die under controlled conditions. Any conventional extruder may be employed to perform the extrusion. The tubing is formed out of the pellets of the selected copolymer typically by extruding at the melt temperature of the selected copolymer materials using a hot feed throat and multiple extruder barrel zones with controlled temperatures. Extrusion conditions are based upon manufacturer's recommended polymer processing conditions.

In one embodiment, the extrusion is carried out using extruder barrel zones of preselected temperature(s). As an example, the temperatures of extruder zones for nylon grades 7128B and 7115U are typically between about 300° F. and about 400° F., and in one embodiment between 330° F. and 370° F. The temperatures of the extruder zones for nylon grades 7024B and 7034B are typically between about 360° F. and about 460° F., and in one embodiment between 380° F. and 430° F. The nylon copolymer material passes out of the extruder barrel and through a clamp and a melt filter before it reaches the extruder die. The clamp, melt filter and two temperature zones within the die are all maintained at the temperature range between 360° F. and 380° F. for nylon grades 7128B and 7115U, and maintained at the temperature range between 430° F. and 450° F. for nylon grades 7024B and 7034B. The melt filter removes foreign matter, which can cause weak imperfections in blown balloons, from the nylon material. After the polymer material is extruded out of the die in tube form it is typically passed through a small air gap and cooled in a water bath. A puller is typically used to pull the extruded tube through the water bath. After passing through the puller, the extruded tubing is cut into sections of predetermined length L, FIG. 1, or is otherwise spooled.

A tubing pre-form process is typically required prior to starting the balloon forming process in order to achieve the desired balloon dimensions of diameter, length, neck wall thickness, and cone wall thickness. During this process, the tubing is selectively stretched in the area N, FIG. 2, where the balloon neck is expected to form upon inflation. The tubing pre-forms, called parisons P (FIG. 2), are formed such that the tubing has sections of varying diameter with the ends of the tubing typically having a smaller or reduced diameter relative to the middle portion of the length of the parison P. The tubing is preferably stretched to form a parison having a selected length PL at about 180 to about 280° F.

In order to form a balloon (FIG. 3) of processed polymer material into a specific size needed for particular blood vessel size/application, a mold having dimensions that allow the parison to blow out to an appropriate predetermined body size BS of selected outer diameter, wall thickness, length BL, FIG. 3, and of predetermined balloon waist inner diameter ID is selected and used to further stretch the tubing. In order to form such a balloon into such a predetermined size, a parison P is typically mounted securely inside a mold mounted within a cooling mechanism such as a waterjacket. An inert gas such as nitrogen is typically applied to the inner lumen of the parison at high pressure with tension applied to the parison axis A. A section of one of the ends of the parison is typically clamped off such that pressure can be maintained inside the parison. The mold is then heated to elevated temperature. A primary stretch along axial direction A is then applied. In one embodiment the parison is stretched 2.0 to 4.0 times its length in the axial direction at about 60 to about 100 degrees Centigrade.

More generally a balloon according to the invention is formed by radial expansion with internal pressure. Preferably, the parison is blown or stretched in the radial direction about 4 to about 8 times its diameter at about 120 to 220° F. under pressure in a range of about 100 to about 350 psi. A secondary stretch along axial direction is then applied to form a cone or conically shaped section C and a neck NK portion of the balloon as shown in FIG. 3. In some embodiments the temperature at the secondary stretch step is the same as the temperature of the primary stretch step. In other embodiments the temperature at the secondary stretch step is 10° F. to 30° F. higher than the temperature of the primary stretch step. Then the mold is heated to elevated temperature ranges for dimensional stabilization (heat setting or thermoforming) of the balloon B to near its radial expanded profile and size by maintaining the balloon at elevated temperature until the selected material is thermally set. The heat setting temperatures can vary with the type of the materials used, the balloon body double wall thickness, and the balloon forming conditions. The typical heat setting temperature is between about 240 to about 280° F., and typically the heat setting heat is applied to the balloon for about 30 seconds to about 2 minutes. After the balloon is heat set, the balloon is cooled for a select period of time, e.g. cooling water is introduced into a water jacket and the mold is cooled from the elevated temperature to room temperature with use of a cooling water recirculation system.

Balloons prepared in this manner are then subjected to standard burst tests by measuring the double body wall thickness of the deflated balloon, inflating the balloon at incrementally increasing pressures and measuring the outside diameter at each increment until the balloon bursts. Any conventional balloon burst system may be employed to perform the burst test. Suitably, an Interface Associate Model LMS-100 system is used. The system offers a non-contact solution to the typical problems encountered in the dimensional measurement of catheter balloons. There is no variability or inaccuracy caused by contact of the measurement device on the soft and compliant balloon. Burst strength, distension and balloon wall strength are calculated from the data obtained.

What is claimed is:

1. A catheter having a balloon comprised of a polymer material comprising:
    first monomer units of an alkyl amide having 2 to 6 carbon atoms; and,
    second monomer units of an alkyl amide having 7 to 12 carbon atoms;
    wherein the first and second monomer units are copolymerized with each other in a random fashion to form a random copolyamide polymer.

2. The catheter of claim 1 wherein the polymer material is formed into a tubular body, the body being stretched about two to about 4 times its relaxed length in the axial direction and blown about 4 to about 8 times its relaxed radius in a radial direction.

3. The catheter of claim 1 wherein one or more of the first monomer units is substituted with between 1 and 5 halogen, amine, nitro and phospho functions.

4. The catheter of claim 1 wherein one or more of the second monomer units is substituted with between 1 and 5 halogen, amine, nitro and phospho functions.

5. The catheter of claim 1 wherein one or more of the first monomer units includes a vinyl function.

6. The catheter of claim 1 wherein one or more of the second monomer units includes a vinyl function.

7. The catheter of claim 1 wherein the first monomer units are straight chained.

8. The catheter of claim 1 wherein the second monomer units are straight chained.

9. The catheter of claim 1 wherein the molar ratio of first to second monomer units is between about 20 and about 80 percent.

10. The catheter of claim 1 wherein the molar ratio first to second monomer units is greater than about 75 percent.

11. The catheter of claim 1 wherein the melting point of the copolymer material is less than about 200 degrees centigrade.

12. A catheter having a balloon comprised of a polymer material comprising:
    first blocks of a homopolymer of monomer units of an alkyl amide having 2 to 6 carbon atoms; and,
    second blocks of a homopolymer of monomer units of an alkyl amide having 7 to 12 carbon atoms;
    wherein the first and second blocks are copolymerized with each other in a random fashion to form a random block copolyamide polymer.

13. The catheter of claim 12 wherein the polymer material is formed into a tubular body, the body being stretched about two to about 4 times its relaxed length in the axial direction and blown about 4 to about 8 times its relaxed radius in a radial direction.

* * * * *